(12) United States Patent
Matsumura et al.

(10) Patent No.: US 9,359,343 B2
(45) Date of Patent: *Jun. 7, 2016

(54) FLUORINE ATOM-CONTAINING DISULFIDE COMPOUND

(71) Applicant: FUJIFILM Corporation, Tokyo (JP)

(72) Inventors: Tokihiko Matsumura, Kanagawa (JP); Yasuaki Matsushita, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/867,259

(22) Filed: Sep. 28, 2015

(65) Prior Publication Data

US 2016/0016922 A1 Jan. 21, 2016

Related U.S. Application Data

(63) Continuation of application No. PCT/JP2014/055938, filed on Mar. 7, 2014.

(30) Foreign Application Priority Data

Mar. 29, 2013 (JP) ................................ 2013-072225

(51) Int. Cl.
C07D 417/12 (2006.01)
C07D 285/125 (2006.01)

(52) U.S. Cl.
CPC .......... C07D 417/12 (2013.01); C07D 285/125 (2013.01)

(58) Field of Classification Search
CPC .................................................... C07D 417/12
See application file for complete search history.

(56) References Cited

U.S. PATENT DOCUMENTS

| | | | |
|---|---|---|---|
| 2005/0191589 A1 | 9/2005 | Loccufier et al. | |
| 2009/0151779 A1 | 6/2009 | Hammami et al. | |
| 2015/0195908 A1 | 7/2015 | Matsushita et al. | |
| 2015/0275029 A1* | 10/2015 | Matsushita | C09D 137/00 428/209 |

FOREIGN PATENT DOCUMENTS

| | | |
|---|---|---|
| DE | 102004008924 A1 | 9/2005 |
| JP | H02-027340 A | 1/1990 |
| JP | H09-071753 A | 3/1997 |
| JP | 2001-019686 A | 1/2001 |
| JP | 2009-531336 A | 9/2009 |
| WO | 2014/045787 A1 | 3/2014 |
| WO | 2014/092044 A1 | 6/2014 |
| WO | WO 2014092044 A1 * | 6/2014 ........... C09D 127/12 |

OTHER PUBLICATIONS

International Search Report from PCT/JP2014/055935 dated Apr. 1, 2104.
International Search Report from PCT/JP2014/055938 dated Apr. 1, 2104.
Translation of the International Preliminary Report on Patentablity mailed on Oct. 8, 2015, which corresponds to PCT/JP2014/055938 and is related to U.S. Appl. No. 14/867,259.
The extended European search report issued by the European Patent Office on Nov. 25, 2015, which corresponds to European Patent Application No. 14773564.1-1462 and is related to U.S. Appl. No. 14/867,259.

* cited by examiner

*Primary Examiner* — Matthew Coughlin
(74) *Attorney, Agent, or Firm* — Studebaker & Brackett PC

(57) ABSTRACT

A disulfide compound represented by formula (1):

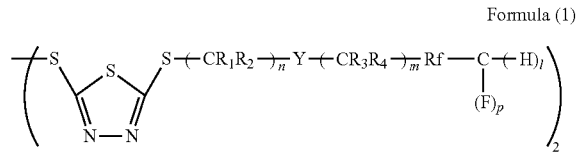

Formula (1)

(in formula (1), $R_1$ and $R_2$ each independently represent a hydrogen atom or an alkyl group; $R_3$ and $R_4$ each independently represent a hydrogen atom or a substituent; Y represents a single bond, —CO— or —COO—; Rf represents a linear or branched perfluoroalkylene group having 1 to 20 carbon atoms or a linear or branched perfluoroether group having 1 to 20 carbon atoms; when Y is a single bond or —CO—, n represents 0 and m represents an integer of 0 to 6; when Y is —COO—, n represents 1 or 2 and m represents an integer of 1 to 6; and p represents an integer of 2 or 3 and l represents an integer of 0 or 1 such that p+l=3).

1 Claim, No Drawings

FLUORINE ATOM-CONTAINING DISULFIDE COMPOUND

CROSS-REFERENCE TO RELATED APPLICATIONS

This application is a Continuation of PCT International Application No. PCT/JP2014/055938 filed on Mar. 7, 2014, which claims priority under 35 U.S.C. §119(a) to Japanese Patent Application No. 2013-072225 filed on Mar. 29, 2013. The above application is hereby expressly incorporated by reference, in its entirety, into the present application.

BACKGROUND OF THE INVENTION

The present invention relates to a fluorine atom-containing disulfide compound and more specifically relates to a fluorine atom-containing disulfide compound having excellent compatibility with a fluorine-containing polymer and a fluorine-containing solvent.

A disulfide compound (compound containing a —S—S— group) is a compound which is important organochemically and physiologically.

For example, it is disclosed that a disulfide compound containing a nitrogen-containing heterocyclic ring (e.g., a thiadiazole ring) has the property of easily forming a chemical bond with or adsorbing metals such as gold, silver and copper in elementary or ionic form and is hence useful as an additive for silver halide photosensitive materials (JP 2-27340 A).

SUMMARY OF THE INVENTION

On the other hand, in recent years, fluorochemical materials (fluorine atom-containing materials) having functions such as durability improvement, surface modification and corrosion protection are industrially widely used. It is possible to impart a variety of functions to such fluorochemical materials if a disulfide compound (in particular a disulfide compound having a thiadiazole ring) can be added thereto.

However, disulfide compounds bleed out from the materials because of their low affinity for fluorine-containing polymers (fluororesins) and fluorine-containing solvents, and hinder production of coating liquids because of their low solubility, and it has been required to improve such problems.

In view of the situation as described above, an object of the present invention is to provide a novel disulfide compound having excellent affinity for a fluorine-containing polymer and a fluorine-containing solvent.

Under these circumstances, the inventors of the present invention have made an intensive study and as a result found a novel disulfide compound having a specific fluorine-containing group in the molecule and thus completed the present invention.

More specifically, the foregoing object is achieved by the following characteristic features.

(1) A compound represented by formula (1) to be described later.

The present invention can provide a novel disulfide compound having excellent affinity for a fluorine-containing polymer and a fluorine-containing solvent.

DETAILED DESCRIPTION OF THE INVENTION

Preferred embodiments of a fluorine atom-containing disulfide compound according to the invention are described below.

Characteristic features of the present invention compared to the conventional art are first described in detail.

Reasons why a disulfide compound having a specific fluorine-containing group in the molecule according to the invention improves the affinity for fluorine-containing polymers and fluorine-containing solvents are not clarified in detail but the mechanism is presumed to be as follows. The disulfide compound of the invention is characterized in that an azole (thiadiazole) ring contains a fluorine-containing group (a perfluoroalkylene group or a perfluoroether group) via a linking group. Having the characteristics as described above, this compound is more likely to form, in a fluorine-containing polymer or a fluorine-containing solvent, a micelle-like structure in which fluorine-containing groups face the surface side and azole rings gather inside and it is therefore presumed that the affinity for the fluorine-containing polymer and the fluorine-containing solvent is improved.

(Compound Represented by Formula (1))

A compound (fluorine atom-containing disulfide compound) represented by formula (1) is described below in detail.

Formula (1)

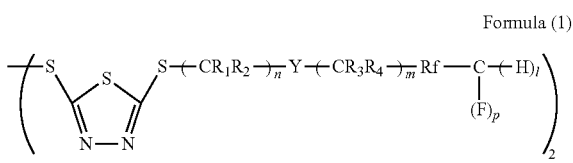

In formula (1), $R_1$ and $R_2$ each independently represent a hydrogen atom or an alkyl group. A plurality of units represented by $CR_1R_2$ may have the same structure or different structures.

When $R_1$ and $R_2$ each represent an alkyl group, the alkyl group preferably contains 1 to 30 carbon atoms, more preferably 1 to 15 carbon atoms and most preferably 1 to 6 carbon atoms. Preferable examples thereof include methyl, ethyl, n-propyl, isopropyl, t-butyl, n-octyl, eicosyl, chloromethyl, hydroxymethyl, aminoethyl, N,N-dimethylaminomethyl, 2-chloroethyl, 2-cyanoethyl, 2-hydroxyethyl, 2-(N,N-dimethylamino)ethyl and 2-ethylhexyl.

As the structure represented by $(CR_1R_2)_n$, —$CH_2$—, —$CH_2CH_2$— and —$CH_2CH(CH_3)$— are preferable, —$CH_2CH_2$— and —$CH_2CH(CH_3)$— are more preferable and —$CH_2CH_2$— is particularly preferable.

$R_3$ and $R_4$ each independently represent a hydrogen atom or a substituent. A plurality of units represented by $CR_3R_4$ may have the same structure or different structures. $R_3$ and $R_4$ may be taken together to form a ring.

The substituents represented by $R_3$ and $R_4$ are, for example, any of the following: halogen atoms (e.g., chlorine atom, bromine atom and iodine atom); alkyl groups [(representing optionally substituted, linear, branched or cyclic alkyl groups including alkyl groups (preferably alkyl groups having 1 to 30 carbon atoms, such as methyl, ethyl, n-propyl, isopropyl, t-butyl, n-octyl, eicosyl, 2-chlorocethyl, 2-cyanoethyl, and 2-ethylhexyl), cycloalkyl groups (preferably optionally substituted cycloalkyl groups having 3 to 30 carbon atoms, such as cyclohexyl, cyclopentyl, and 4-n-dodecyl cyclohexyl), and bicycloalkyl groups (preferably optionally substituted bicycloalkyl groups having 5 to 30 carbon atoms, i.e., monovalent groups obtained by removing one hydrogen atom from bicycloalkanes having 5 to 30 carbon atoms, such as bicyclo[1,2,2]heptan-2-yl, bicyclo[2,2,2]octan-3-yl) and also including tricyclic structures containing a large number of ring structures; alkyl groups in substituents to be illustrated below (e.g., an alkyl group in an alkylthio group) also representing the alkyl groups of the concept given above];

alkenyl groups [representing optionally substituted, linear, branched or cyclic alkenyl groups including alkenyl groups (preferably optionally substituted alkenyl groups having 2 to 30 carbon atoms, such as vinyl, allyl, prenyl, geranyl, and oleyl), cycloalkenyl groups (preferably optionally substituted cycloalkenyl groups having 3 to 30 carbon atoms, i.e., monovalent groups obtained by removing one hydrogen atom from cycloalkenes having 3 to 30 carbon atoms, such as 2-cyclopenten-1-yl, and 2-cyclohexen-1-yl), and bicycloalkenyl groups (optionally substituted bicycloalkenyl groups, preferably optionally substituted bicycloalkenyl groups having 5 to 30 carbon atoms, i.e., monovalent groups obtained by removing one hydrogen atom from bicycloalkenes having a double bond, including, for example, bicyclo[2,2,1]hept-2-en-1-yl, and bicyclo[2,2,2]oct-2-en-4-yl)], alkynyl groups (preferably optionally substituted alkynyl groups having 2 to 30 carbon atoms, such as ethynyl, propargyl and trimethylsilylethynyl groups);

aryl groups (preferably optionally substituted aryl groups having 6 to 30 carbon atoms, such as phenyl, p-tolyl, naphthyl, m-chlorophenyl, and o-hexadecanoylaminophenyl), heterocyclic groups (preferably optionally substituted, 5- or 6-membered monovalent groups obtained by removing one hydrogen atom from aromatic or non-aromatic heterocyclic compounds, and more preferably 5- or 6-membered heteroaromatic ring groups having 3 to 30 carbon atoms, such as 2-furanyl, 2-thienyl, 2-pyrimidinyl and 2-benzothiazolyl);

cyano group, hydroxyl group, nitro group, carboxyl group, alkoxy groups (preferably optionally substituted alkoxy groups having 1 to 30 carbon atoms, such as methoxy, ethoxy, isopropoxy, t-butoxy, n-octyloxy, and 2-methoxyethoxy), aryloxy groups (preferably optionally substituted aryloxy groups having 6 to 30 carbon atoms, such as phenoxy, 2-methylphenoxy, 4-t-butylphenoxy, 3-nitrophenoxy, and 2-tetradecanoylaminophenoxy), silyloxy groups (preferably silyloxy groups having 3 to 20 carbon atoms, such as trimethylsilyloxy, and t-butyldimethylsilyloxy), heterocyclic oxy groups (preferably optionally substituted heterocyclic oxy groups having 2 to 30 carbon atoms, 1-phenyltetrazol-5-oxy, and 2-tetrahydropyranyloxy), acyloxy groups (preferably formyloxy group, optionally substituted alkylcarbonyloxy groups having 2 to 30 carbon atoms, and optionally substituted arylcarbonyloxy groups having 6 to 30 carbon atoms, such as formyloxy, acetyloxy, pivaloyloxy, stearoyloxy, benzoyloxy, and p-methoxyphenylcarbonyloxy), carbamoyloxy groups (preferably optionally substituted carbamoyloxy groups having 1 to 30 carbon atoms, such as N,N-dimethylcarbamoyloxy, N,N-diethylcarbamoyloxy, morpholinocarbonyloxy, N,N-di-n-octylaminocarbonyloxy, and N-n-octylcarbamoyloxy), alkoxycarbonyloxy groups (preferably optionally substituted alkoxycarbonyloxy groups having 2 to 30 carbon atoms, such as methoxycarbonyloxy, ethoxycarbonyloxy, t-butoxycarbonyloxy, and n-octylcarbonyloxy), aryloxycarbonyloxy groups (preferably optionally substituted aryloxycarbonyloxy groups having 7 to 30 carbon atoms, such as phenoxycarbonyloxy, p-methoxyphenoxycarbonyloxy, and p-n-hexadecyloxyphenoxycarbonyloxy);

amino groups (preferably amino group, optionally substituted alkylamino groups having 1 to 30 carbon atoms, and optionally substituted anilino groups having 6 to 30 carbon atoms, such as amino, methylamino, dimethylamino, anilino, N-methyl-anilino and diphenylamino), acylamino groups (preferably formylamino group, optionally substituted alkylcarbonylamino groups having 1 to 30 carbon atoms, and optionally substituted arylcarbonylamino groups having 6 to 30 carbon atoms, such as formylamino, acetylamino, pivaloylamino, lauroylamino, benzoylamino, and 3,4,5-tri-n-octyloxyphenylcarbonylamino), aminocarbonylamino groups (preferably optionally substituted aminocarbonylamino having 1 to 30 carbon atoms, such as carbamoylamino, N,N-dimethylaminocarbonylamino, N,N-diethylaminocarbonylamino, and morpholinocarbonylamino), alkoxycarbonylamino groups (preferably optionally substituted alkoxycarbonylamino groups having 2 to 30 carbon atoms, such as methoxycarbonylamino, ethoxycarbonylamino, t-butoxycarbonylamino, n-octadecyloxycarbonylamino, and N-methyl-methoxycarbonylamino), aryloxycarbonylamino groups (preferably optionally substituted aryloxycarbonylamino groups having 7 to 30 carbon atoms, such as phenoxycarbonylamino, p-chlorophenoxycarbonylamino, and m-n-octyloxyphenoxycarbonylamino), sulfamoylamino groups (preferably optionally substituted sulfamoylamino groups having 0 to 30 carbon atoms, such as sulfamoylamino, N,N-dimethylaminosulfonylamino, and N-n-octylaminosulfonylamino), alkyl- and arylsulfonylamino groups (preferably optionally substituted alkylsulfonylamino having 1 to 30 carbon atoms, and optionally substituted arylsulfonylamino having 6 to 30 carbon atoms, such as methylsulfonylamino, butylsulfonylamino, phenylsulfonylamino, 2,3,5-trichlorophenylsulfonylamino, and p-methylphenylsulfonylamino);

mercapto group, alkylthio groups (preferably optionally substituted alkylthio groups having 1 to 30 carbon atoms, such as methylthio, ethylthio, and n-hexadecylthio), arylthio groups (preferably optionally substituted arylthio having 6 to 30 carbon atoms, such as phenylthio, p-chlorophenylthio, and m-methoxyphenylthio), heterocyclic thio groups (preferably optionally substituted heterocyclic thio groups having 2 to 30 carbon atoms, such as 2-benzothiazolylthio, and 1-phenyltetrazol-5-ylthio), sulfamoyl groups (preferably optionally substituted sulfamoyl groups having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N-(N'-phenylcarbamoyl)sulfamoyl), sulfo group, alkyl- and arylsulfinyl groups (preferably optionally substituted alkylsulfinyl groups having 1 to 30 carbon atoms, and optionally substituted arylsulfinyl groups having 6 to 30 carbon atoms, such as methylsuifinyl, ethylsulfinyl, phenylsulfinyl and p-methylphenylsulfinyl);

alkyl- and arylsulfonyl groups (preferably optionally substituted alkylsulfonyl groups having 1 to 30 carbon atoms, and optionally substituted arylsulfonyl groups having 6 to 30 carbon atoms, such as methylsulfonyl, ethylsulfonyl, phenylsulfonyl, and p-methylphenylsulfonyl), acyl groups (preferably formyl group, optionally substituted alkylcarbonyl groups having 2 to 30 carbon atoms, optionally substituted arylcarbonyl groups having 7 to 30 carbon atoms, and optionally substituted heterocyclic carbonyl groups having 4 to 30 carbon atoms in which a carbonyl group is bonded to a carbon atom, such as acetyl, pivaloyl, 2-chloroacetyl, stearoyl, benzoyl, p-n-octyloxyphenylcarbonyl, 2-pyridylcarbonyl, and 2-furylcarbonyl), aryloxycarbonyl groups (preferably optionally substituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl), alkoxycarbonyl groups (preferably optionally substituted alkoxycarbonyl groups having 2 to 30 carbon atoms, such as methoxycarbonyl, ethoxycarbonyl, t-butoxycarbonyl, and n-octadecyloxycarbonyl); and carbamoyl groups (preferably optionally substituted carbamoyl having 1 to 30 carbon atoms, such as carbamoyl, N-methylcarbamoyl, N,N-dimethylcarbamoyl, N,N-di-n-octylcarbamoyl, and N-(methylsulfonyl)carbamoyl), aryl- and heterocyclic azo groups (preferably optionally substituted arylazo groups having 6 to 30 carbon atoms, and optionally substituted heterocyclic azo groups having 3 to 30 carbon atoms, such as phenylazo, p-chlorophenylazo, and 5-ethylthio-1,3,4-thiadiazol-2-ylazo), imide groups (preferably N-succinimide, and N-phthalimide), phosphino groups (preferably optionally substituted phosphino groups having 2 to 30 carbon atoms, such as dimethylphosphino, diphenylphosphino, and methylphenoxyphosphino), phosphinyl groups (preferably optionally substituted phosphinyl groups having 2 to 30 carbon atoms, such as phosphinyl, dioctyloxyphosphinyl, and diethoxyphosphinyl), phosphinyloxy groups (preferably optionally substituted phosphinyloxy groups having 2 to 30 carbon atoms, such as diphenoxyphosphinyloxy, and dioctyloxyphosphinyloxy), phosphinylamino groups (preferably optionally substituted phosphinylamino groups having 2 to 30 carbon atoms, such as dimethoxyphosphinylamino, and dimethylaminophosphinylamino), silyl groups (preferably optionally substituted silyl groups having 3 to 30 carbon atoms, such as trimethylsilyl, t-butyldimethylsilyl, and phenyldimethylsilyl).

Of the foregoing functional groups, ones having a hydrogen atom may be further substituted with any of the foregoing groups after removal of the hydrogen atom.

As the structure represented by $(CR_3R_4)_m$, $-CH_2-$, $-CH_2CH_2-$, $-CH_2CH(CH_3)-$, $-CH_2CH_2CH_2-$, $-CH_2CH(OH)CH_2-$ and $-CH_2CH(CH_2OH)-$ are preferable, $-CH_2-$, $-CH_2CH_2-$, $-CH_2CH(OH)CH_2-$ and $-CH_2CH_2CH_2-$ are more preferable, and $-CH_2-$ and $-CH_2CH_2-$ are particularly preferable.

Y represents a single bond, $-CO-$ or $-COO-$.

When Y is a single bond or $-CO-$, n represents 0 and m represents an integer of 0 to 6. Above all, m is preferably 0 to 4 and more preferably 1 or 2.

When Y is $-COO-$, n represents 1 or 2 and preferably 2. m represents an integer of 1 to 6, preferably 1 to 4, and more preferably 1 or 2.

Rf represents a linear or branched perfluoroalkylene group having 1 to 20 carbon atoms or a linear or branched perfluoroether group having 1 to 20 carbon atoms.

Although the perfluoroalkylene group contains 1 to 20 carbon atoms, the number of carbons in the perfluoroalkylene group is preferably 2 to 15, and more preferably 3 to 12 in terms of more excellent affinity for a fluorine-containing polymer and a fluorine-containing solvent. Specific examples of the perfluoroalkylene group include $C_4F_8-$, $C_5F_{10}-$, $C_6F_{12}-$, $C_7F_{14}-$, $C_8F_{16}-$, $C_9F_{18}-$, $C_{10}F_{20}-$ and $C_{12}F_{24}-$.

The perfluoroether group refers to a group in which an ethereal oxygen atom ($-O-$) is inserted between carbon atoms at one or more moieties in the perfluoroalkylene group or at the bond terminal of the perfluoroalkylene group. Although the perfluoroether group contains 1 to 20 carbon atoms, the number of carbons in the perfluoroether group is preferably 2 to 15, and more preferably 3 to 12 in terms of more excellent affinity for a fluorine-containing polymer and a fluorine-containing solvent. Specific examples of the perfluoroether group include perfluoroether groups represented by $-(C_gF_{2g}O)_h-$ (where each g is independently an integer of 1 to 20 and h is an integer of 1 or more such that $g \times h \leq 20$).

p represents an integer of 2 or 3 and l represents an integer of 0 or 1 such that p+l=3. Above all, p and l preferably represent 3 and 0, respectively, in terms of more excellent affinity for a fluorine-containing polymer and a fluorine-containing solvent.

Examples of the compound represented by formula (1) according to the invention are illustrated below but the present invention is not limited thereto.

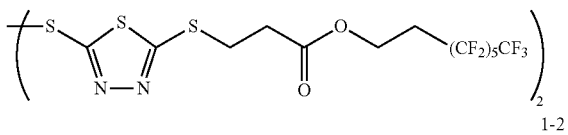

1-1

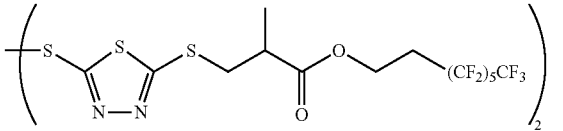

1-2

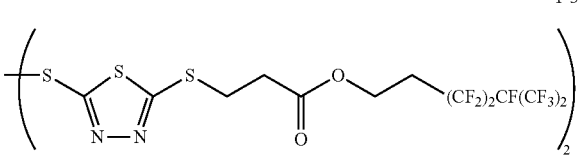

1-3

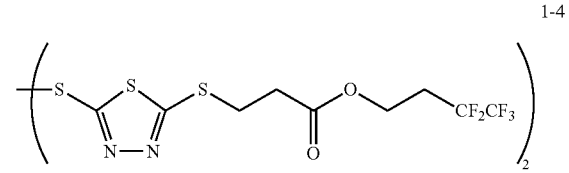

1-4

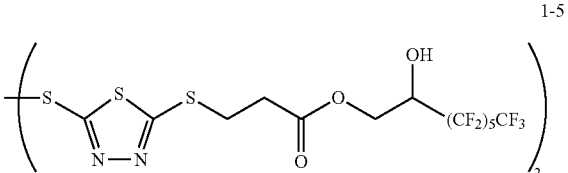

1-5

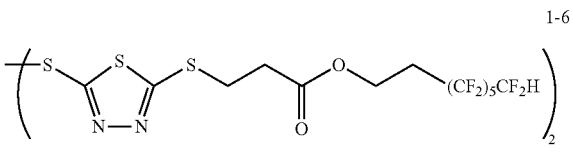

1-6

(Method of Producing Compound Represented by Formula (1))

The method of producing the compound represented by formula (1) is not particularly limited and the compound represented by formula (1) can be produced by combining known methods.

For example, the compound represented by formula (1) can be produced by a process shown in Scheme 1 or Scheme 2 below but the production method is not limited thereto.

The procedure of each of Schemes is described below in detail.

(Scheme 1)

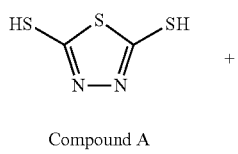

Compound A

-continued

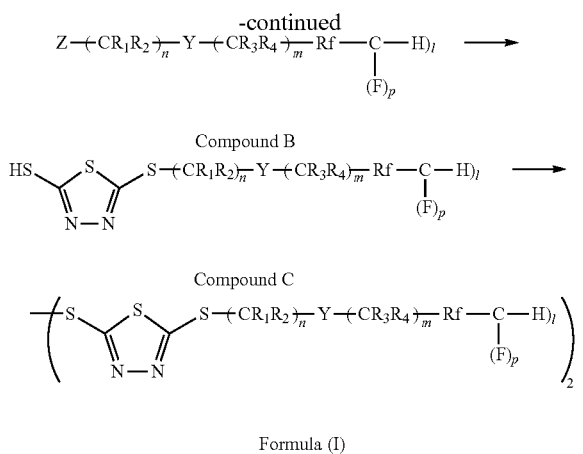

Formula (I)

In Scheme 1, a compound A (1,3,4-thiadiazole-2,5-dithiol) and a compound B having a leaving group Z are prepared and reacted together to produce a compound C, and the compounds C are bonded together by an oxidation reaction to produce a desired compound represented by formula (1).

The type of the leaving group Z in the compound B is not particularly limited and preferable examples of the leaving group include chlorine atom, bromine atom, iodine atom, fluorine atom, methanesulfonyloxy group, benzenesulfonyloxy group, p-toluenesulfonyloxy group, trifluoromethanesulfonyloxy group and nonafluorobutanesulfonyloxy group.

The compound A may be reacted with the compound B in the presence of a base if necessary. Any known compound can be used as the base for use in the reaction and the base is preferably selected from among, for example, organic bases (e.g., triethylamine, trimethylamine, diisopropylethylamine, pyridine, morpholine, 1,4-diazabicyclo[2,2,2]octane, 1,5-diazabicyclo[4.3.0]non-5-ene, 1,8-diazabicyclo[5.4.0]undec-7-ene, sodium methoxide, potassium methoxide, sodium ethoxide, potassium ethoxide, butyllithium, t-butyllithium, and sec-butyllithium), and inorganic bases (e.g., sodium carbonate, potassium carbonate, sodium hydrogen carbonate, potassium hydrogen carbonate, sodium hydroxide, potassium hydroxide, lithium hydroxide, cesium hydroxide, calcium hydroxide, potassium hydride, sodium hydride and lithium aluminum hydride).

It should be noted that the foregoing reaction may be carried out in the presence of a solvent if necessary. The type of the solvent to be used is not particularly limited and examples thereof include water and organic solvents.

Although the conditions of the reaction between the compound A and the compound B are not particularly limited, a heating treatment is preferably carried out at 0 to 150° C. (more preferably 20 to 100° C.) for 1 to 48 hours (more preferably for 2 to 24 hours) in terms of the balance between the productivity and the yield.

Next, unreacted materials, by-products and other impurities are separated for refinement if necessary to obtain a compound C. Separation and refinement need only be performed by a common method, and examples thereof include an extraction operation using an organic solvent, recrystallization, crystallization using a poor solvent, and column chromatography using silica gel.

Next, mercapto groups in the compound C are bonded together in the presence of an oxidizing agent to produce a compound represented by formula (1).

The type of the oxidizing agent that can be used is not particularly limited and peroxides (organic peroxides and inorganic peroxides) are preferably used, as exemplified by hydrogen peroxide, tert-butyl hydroperoxide, meta-chloroperoxybenzoic acid, and peracetic acid.

If necessary, the reaction is preferably carried out in the presence of iodide ions as the catalyst. Exemplary iodine-containing compounds that may give iodide ions serving as the catalyst include iodine; metal salts such as sodium iodide, and potassium iodide; and quaternary ammonium salts such as tetraethylammonium iodide and tetrabutylammonium iodide. Of these, sodium iodide is preferable in terms of versatility and obtention of a disulfide compound at a high yield.

Although the conditions of the reaction between the foregoing compounds C are not particularly limited, a heating treatment is preferably carried out at −20° C. to 100° C. (more preferably 0 to 60° C.) for 0.5 to 48 hours (more preferably for 1 to 24 hours) in terms of the balance between the productivity and the yield.

After the end of the reaction, unreacted materials, by-products and other impurities are separated for refinement if necessary to obtain the compound represented by formula (1). Separation and refinement need only be performed by a common method, and examples thereof include an extraction operation using an organic solvent, recrystallization, crystallization using a poor solvent, and column chromatography using silica gel.

$R_1$, $R_2$, $R_3$ and $R_4$ as well as n, m, l and p of the compounds B and C in Scheme 1 are as defined above.

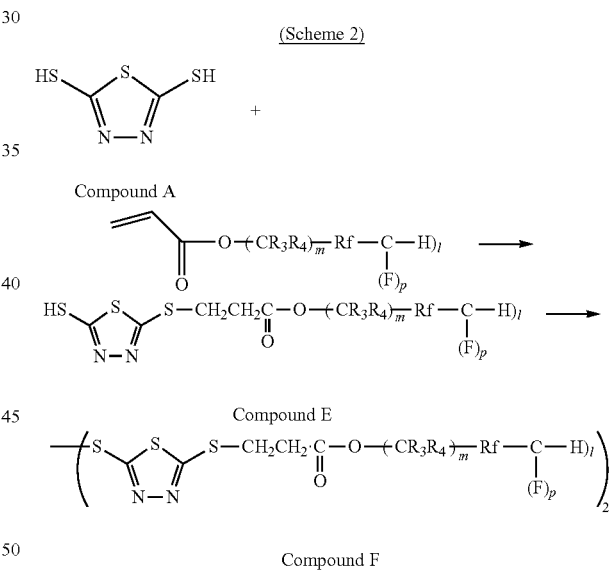

In Scheme 2, a compound A and a compound D having an acryloyl group (acrylic acid ester) are prepared and reacted together to produce a compound E, and the compounds E are then bonded together by an oxidation reaction to produce a desired compound F corresponding to the compound represented by formula (1).

The compound A may be reacted with the compound D in the presence of a solvent if necessary. The type of the solvent to be used is not particularly limited and examples thereof include water and organic solvents.

If necessary, the foregoing reaction may be carried out in the presence of a base as illustrated in Scheme 1.

If necessary, various types of separation and refinement described in Scheme 1 may be carried out after the end of the reaction.

Although the conditions of the reaction between the compound A and the compound D are not particularly limited, a heating treatment is preferably carried out at 0 to 150° C. (more preferably 20 to 100° C.) for 1 to 48 hours (more preferably for 2 to 24 hours) in terms of the balance between the productivity and the yield.

The oxidation reaction between the compounds E is preferably carried out according to the procedure of the oxidation reaction between the compounds C as described in Scheme 1.

$R_3$ and $R_4$ as well as m, l and p of the compounds D, E and F in Scheme 2 are as defined above.

The compound represented by formula (1) can be used in various applications.

In addition, the compound represented by formula (1) has excellent affinity for a fluorine-containing polymer (fluororesin) and a fluorine-containing solvent. Examples of the fluorine-containing polymer include known fluorine atom-containing polymers (e.g., polytetrafluoroethylene, polyvinylidene fluoride, polyvinyl fluoride, and a cyclized polymer of perfluoro(butenyl vinyl ether) (Cytop (registered trademark))). The fluorine-containing polymer may also be a polymer obtained by polymerizing a fluorine-containing ethylenic monomer. Examples of the fluorine-containing ethylenic monomer include vinylidene fluoride, tetrafluoroethylene, hexafluoropropylene, vinyl trifluorochloride, vinyl fluoride, perfluoroalkyl vinyl ether, fluorine-containing (meth)acrylic monomers (e.g., 1H,1H,2H,2H-heptadecafluorodecyl methacrylate, 1H,1H,5H-octafluoropentyl methacrylate, 2,2,3,3-tetrafluoropropyl methacrylate, 2,2,2-trifluoroethyl methacrylate, 1H,1H,2H,2H-heptadecafluorodecyl acrylate, 1H,1H,5H-octafluoropentyl acrylate, 2,2,3,3-tetrafluoropropyl acrylate, 2,2,2-trifluoroethyl acrylate, perfluorooctyl ethyl methacrylate, and perfluorooctyl ethyl acrylate).

An example of the fluorine-containing solvent includes a known fluorine atom-containing solvent. Examples of the fluorine-containing solvent include a fluorine-modified aliphatic hydrocarbon solvent, a fluorine-modified aromatic hydrocarbon solvent, a fluorine-modified ether solvent, and a fluorine-modified alkylamine solvent. Specific examples of the fluorine-containing solvent that may be illustrated include polyfluorotrialkylamine compounds (fluorine-modified alkylamine solvents) such as perfluorobenzene, pentafluorobenzene, 1,3-bis(trifluoromethyl)benzene, 1,4-bis(trifluoromethyl)benzene, perfluorotributylamine, perfluorotripropylamine and perfluorotripentylamine; fluorine-modified aliphatic hydrocarbon solvents such as perfluorodecalin, perfluorocyclohexane, perfluoro(1,3,5-trimethylcyclohexane), perfluoro(2-butyltetrahydrofuran), perfluorohexane, perfluorooctane, perfluorodecane, perfluorododecane, perfluoro(2,7-dimethylocrane), 1,1,2-trichloro-1,2,2-trifluoroethane, 1,1,1-trichloro-2,2,2-trifluoroethane, 1,3-dichloro-1,1,2,2,3-pentafluoropropane, 1,1,1,3-tetrachloro-2,2,3,3-tetrafluoropropane, 1,1,3,4-tetrachloro-1,2,2,3,4,4-hexafluorobutane, perfluoro(1,2-dimethylhexane), perfluoro(1,3-dimethylhexane), 2H,3H-perfluoropentane, 1H-perfluorohexane, 1H-perfluorooctane, 1H-perfluorodecane, 1H,1H,1H,2H,2H-perfluorohexane, 1H,1H,1H,2H,2H-perfluorooctane, 1H,1H,1H,2H,2H-perfluorodecane, 3H,4H-perfluoro-2-methylpentane, 2H,3H-perfluoro-2-methylpentane, 1H-1,1-dichloroperfluoropropane, 1H-1,3-dichloroperfluoropropane, and perfluoroheptane; fluorine-modified aromatic hydrocarbon solvents such as m-xylene trifluoride, m-xylene hexafluoride and benzotrifluoride; and fluorine-modified ether solvents such as methyl perfluorobutyl ether, and perfluoro(2-butyltetrahydrofuran).

EXAMPLES

The present invention is described below in further detail by way of examples. However, the invention should not be construed as being limited to the following examples. Unless otherwise specified, the ratio is expressed by percentage by weight.

Example 1

Synthesis of Compound 1-1

Compound 1-1A was synthesized according to the following scheme.

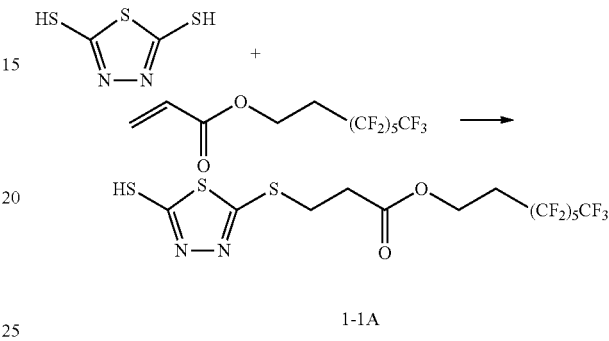

1-1A 1,3,4-Thiadiazole-2,5-dithiol (manufactured by Wako Pure Chemical Industries, Ltd.) (4.0 g; 26.6 mmol) and tetrahydrofuran (80 mL) were introduced into a reaction vessel and completely dissolved. 3,3,4,4,5,5,6,6,7,7,8,8,8-Tridecafluorooctyl acrylate (11.13 g; 26.6 mmol) was added dropwise from a dropping funnel over 0.5 hour. After stirring at 65° C. for 6 hours, the solution was cooled to room temperature and concentrated under reduced pressure. Hexane (200 mL) was added to the reaction mixture and the mixture was cooled in an ice bath to obtain 15 g of crude crystals. A portion of the crude crystals (7.5 g) was purified by silica gel column chromatography (mobile phase: hexane/ethyl acetate=2/1 to 1/1) to obtain 6 g of Compound 1-1A (yield: 79%).

Next, the resulting Compound 1-1A was used to synthesize Compound 1-1 according to the following scheme.

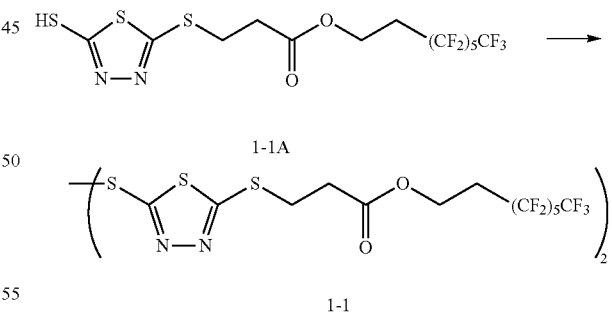

1-1

Compound 1-1A (3.0 g; 5.28 mmol) and ethyl acetate (20 mL) were introduced into a reaction vessel and completely dissolved. Sodium iodide (79.1 mg; 0.528 mmol) and 30% hydrogen peroxide (22.11 mmol; 2.39 g) were added in this order and the mixture was stirred at room temperature for 1 hour. The precipitated crystals were washed with 100 mL of water and the resulting crude crystals (2.7 g) were purified by silica gel column chromatography (mobile phase: hexane/ethyl acetate=2/1 to 1/1) to obtain 2.4 g of Compound 1-1 according to the invention (yield: 80%).

The resulting Compound 1-1 according to the invention had the following NMR spectrum:

¹H-NMR (solvent: deuterated chloroform; reference: tetramethylsilane): 4.43 (2H,t), 3.60(2H,t), 2.95(2H,t), 2.49(2H,m)

The resulting compound was identified as Compound 1-1 of the invention because each proton peak was observed at a characteristic position in the ¹H-NMR data.

The synthesis method of Example 1 and a method known in a literature were used to synthesize Compounds 1-2 to 1-6 illustrated above as specific examples of the compound represented by formula (1) in the same manner.

<Evaluation of Solubility>
(Testing Method)

To a mixed solution of perfluorotributylamine/1,1,1,3,3,3-hexafluoropropan-2-ol/Cytop CTL-809M (manufactured by Asahi Glass Co., Ltd.) (85/10/5), was added the compound represented by formula (1) according to the invention (any of Compounds 1-1 to 1-6) or any of Comparative Compounds C-1 to C-3 as shown below in an amount of 0.1 wt %, 0.25 wt %, 0.5 wt % or 1.0 wt % with respect to the Cytop CTL-809M. Thereafter, the mixed solution was applied onto a glass substrate to a film thickness of 2 μm and dried.

The surface profile of the resulting coated film was observed by an optical microscope to check whether each compound bled out or remained partially undissolved. An evaluation was made based on the following criteria:

A: The compound neither remained partially undissolved nor bled out in an amount of 1.0 wt %.
B: The compound was compatible in an amount of up to 0.5 wt % but remained partially undissolved or bled out in an amount of 1.0 wt %.
C: The compound was compatible in an amount of up to 0.25 wt % but remained partially undissolved or bled out in an amount of 0.5 wt %.
D: The compound was compatible in an amount of up to 0.1 wt % but remained partially undissolved or bled out in an amount of 0.25 wt %.
E: The compound did not remain partially undissolved but bled out in an amount of 0.1 wt %.
F: The compound was not compatible and remained partially undissolved in an amount of 0.1 wt %.

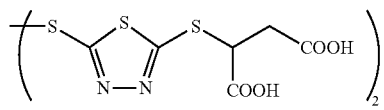
C-1

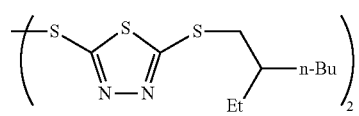
C-2

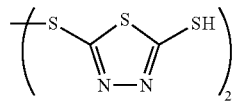
C-3

TABLE 1

| Compound | Solubility | Remarks |
| --- | --- | --- |
| Compound 1-1 | A | Present invention |
| Compound 1-2 | A | Present invention |
| Compound 1-3 | A | Present invention |
| Compound 1-4 | C | Present invention |
| Compound 1-5 | B | Present invention |
| Compound 1-6 | C | Present invention |
| C-1 | F | Comparative example |
| C-2 | E | Comparative example |
| C-3 | F | Comparative example |

When Comparative Compounds C-1 to C-3 free from a fluorine-containing alkyl group were used, the compounds remained partially undissolved or bled out in an amount of 0.1 wt %.

In contrast, the compounds of formula (1) according to the invention are found to exhibit excellent compatibility with resin and to have high affinity for fluorine materials. Higher affinity for fluorine materials was confirmed particularly in Compounds 1-1 to 1-3 in which p is 3, 1 is 0 and $R_3$ and $R_4$ are each a hydrogen atom, the perfluoroalkylene group contained having 5 or more carbon atoms.

What is claimed is:

1. A compound represented by formula (1):

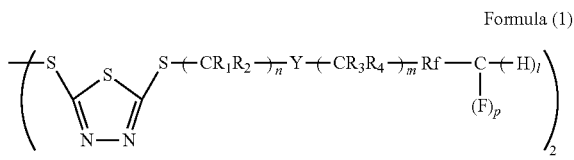

Formula (1)

(wherein $R_1$ and $R_2$ each independently represent a hydrogen atom or an alkyl group; $R_3$ and $R_4$ each independently represent a hydrogen atom or a substituent; Y represents a single bond, —CO— or —COO—; Rf represents a linear or branched perfluoroalkylene group having 1 to 20 carbon atoms or a linear or branched perfluoroether group having 1 to 20 carbon atoms; when Y is a single bond or —CO—, n represents 0 and m represents an integer of 0 to 6; when Y is —COO—, n represents 1 or 2 and m represents an integer of 1 to 6; and p represents an integer of 2 or 3 and 1 represents an integer of 0 or 1 such that p+1=3).

* * * * *